(12) United States Patent
Saito et al.

(10) Patent No.: US 8,227,775 B2
(45) Date of Patent: Jul. 24, 2012

(54) PARTICLE BEAM THERAPY SYSTEM

(75) Inventors: Kazuyoshi Saito, Hitachi (JP); Hiroaki Sakurabata, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 66 days.

(21) Appl. No.: 12/252,448

(22) Filed: Oct. 16, 2008

(65) Prior Publication Data

US 2009/0114852 A1    May 7, 2009

(30) Foreign Application Priority Data

Nov. 6, 2007   (JP) .................................. 2007-288002

(51) Int. Cl.
*A61N 5/00* (2006.01)
(52) U.S. Cl. .............. 250/492.3; 250/492.21; 250/505.1
(58) Field of Classification Search ................. 250/492.3
See application file for complete search history.

(56) References Cited

U.S. PATENT DOCUMENTS

| | | | |
|---|---|---|---|
| 5,363,008 A | 11/1994 | Hiramoto et al. | |
| 7,122,978 B2 * | 10/2006 | Nakanishi et al. | 315/500 |
| 7,576,342 B2 * | 8/2009 | Hiramoto et al. | 250/492.3 |
| 2004/0227104 A1 | 11/2004 | Matsuda et al. | |

FOREIGN PATENT DOCUMENTS

| | | |
|---|---|---|
| EP | 0 779 081 | 6/1997 |
| JP | 2596292 | 1/1997 |
| JP | 2833602 | 10/1998 |
| JP | 3874766 | 11/2006 |

OTHER PUBLICATIONS

T. Wangler, "Beam Halo in High-Intensity Beams", Computational Accelerator Physics Conference, Feb. 1993.*
M. Ikegami, "Particle-Core Analysis of Beam Halos in a Synchrotron", Proceedings 1999 Particle Accelerator Conference, NY, 1999.*
U.S. Appl. No. 12/190,909, filed Aug. 13, 2008, Saito et al.

* cited by examiner

*Primary Examiner* — Phillip A Johnston
(74) *Attorney, Agent, or Firm* — Mattingly & Malur, PC (57) ABSTRACT

A particle beam therapy system includes a synchrotron which accelerates beams of charged particles to a desired energy level and permits extraction of the beams of charged particles exceeding a stability limit, an irradiation device which irradiates an object with the beams of charged particles, a beam transport system which conducts the beams of charged particles extracted from the synchrotron to the irradiation device, and a control unit which provides control to remove part of the beams of charged particles circling in the synchrotron and allow the rest of the circling beams of charged particles to be extracted from the synchrotron and conducted to the irradiation device. The particle beam therapy system produces irradiation beams suitable for high-precision particle beam therapy by the spot scanning method or the like.

5 Claims, 10 Drawing Sheets

PARTICLE BEAM THERAPY SYSTEM

BACKGROUND OF THE INVENTION

1. Field of the Invention

The present invention relates to a particle beam therapy system which is provided with a synchrotron and is capable of precision irradiation for treatment.

2. Description of the Related Art

In the recent aging society, the radiotherapy for cancer treatment is attracting attentions because of its non-invasive nature and its good therapeutic effect for patients to maintain their high quality of life after treatment. Among various radiotherapy systems, the particle beam therapy system, which employs ion beams or beams of charged particles (such as protons or carbon atoms) accelerated by an accelerator, is considered particularly promising because of its ability to highly concentrate beams to the affected part. The particle beam therapy system is composed of an accelerator, a beam transport system, and an irradiation device. The first is a synchrotron or the like which accelerates beams of charged particles emerging from an ion source up to nearly the velocity of light. The second transports the beams of charged particles which have been extracted from the accelerator. The third irradiates a patient with beams of charged particles in a specific way according to the position and shape of the affected part. (See Patent Document 1.)

The conventional irradiation device attached to the particle beam therapy system expands the beam diameter by means of a scatterer and then scrapes off the periphery by means of a collimater to shape the beams of charged particles before irradiation with the beams of charged particles conforming to the shape of the affected part. Unfortunately, the irradiation method that employs a scatterer needs to improve the beam availability, to reduce the generation of neutrons, and to improve conformity between the irradiation region and the shape of the affected part. This has recently aroused a need for a method of more accurate irradiation, which is called scanning irradiation method. This method is made up of extracting thin beams of charged particles from an accelerator, deflecting them by means of electromagnets, and scanning the affected part with them in conformity with its shape.

The scanning irradiation method works to irradiate irradiation spots SP defined by division of the three-dimensional affected part into layers and further division of each layer into small segments. Layers in the depthwise direction are selectively irradiated with the beams of charged particles whose energy level is properly adjusted. Spots in each layer are irradiated with the beams of charged particles at a desired dose by two-dimensional scanning with electromagnets. The irradiation beams may be kept on or turned off during movement from one irradiation spot SP to another. These procedures are called raster scanning and spot scanning, respectively. The latter is disclosed in Patent Document 2.

Figure 8:
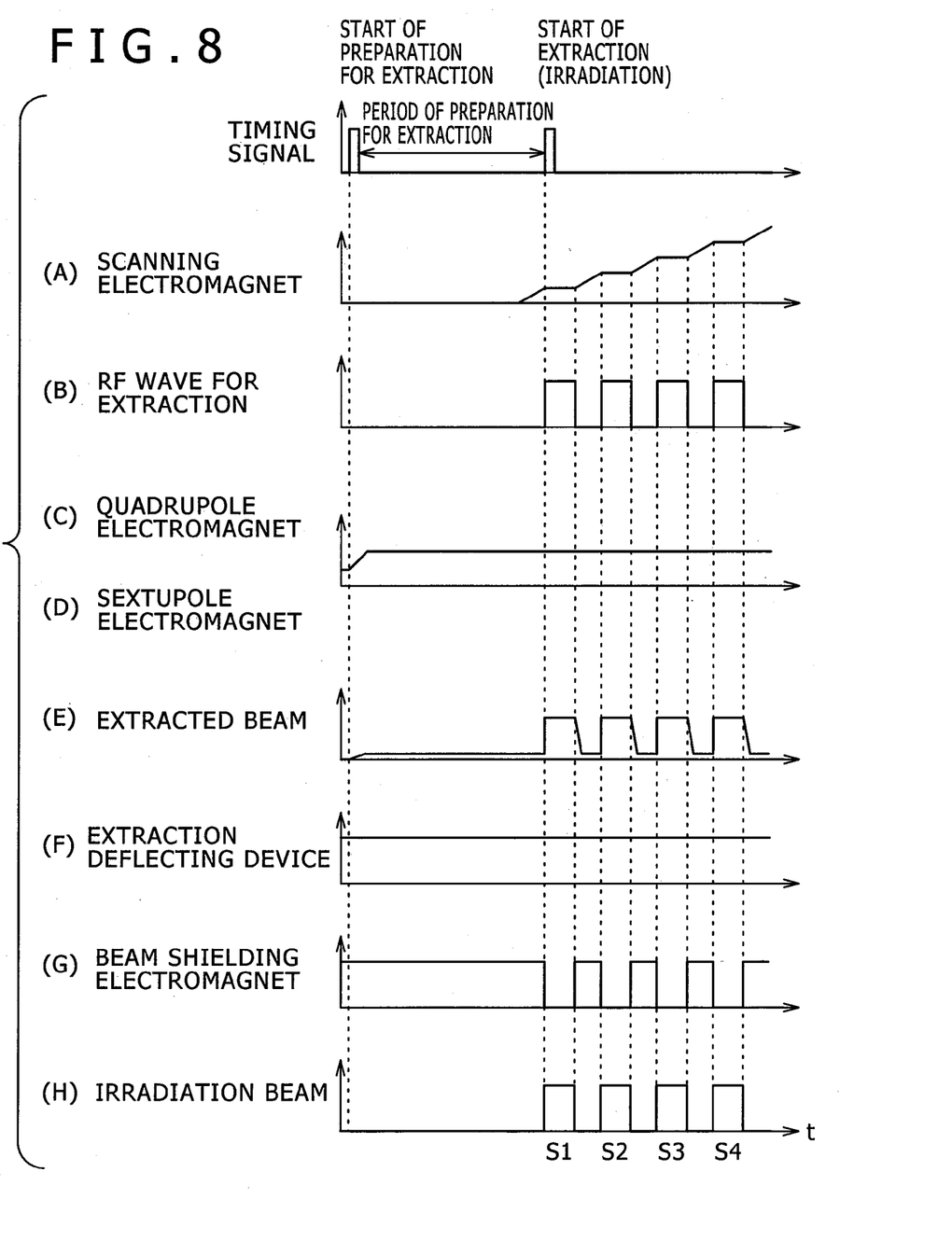
FIG. 8 is a timing chart showing the operation sequence of a conventional particle beam therapy system.

The conventional spot scanning method will be described below with reference to FIG. 8. FIG. 8 shows the extraction preparing period that follows the completion of acceleration and the timing chart immediately after the start of extraction, which are involved in the operating sequence of the particle beam therapy system that employs the spot scanning method. The spot scanning method is made up of irradiating the irradiation spots sequentially one after another. While one spot is being irradiated at a prescribed dose, the beam scanning is suspended. The beam scanning is resumed, with the beams of charged particles turned off, and the adjacent spot is irradiated. Movement from one spot to another is accomplished by adjusting the amount of excitation for the scanning electromagnet. Irradiation in this manner determines the total dose to the affected part (or the irradiation field) in terms of the superposition of individual doses to individual irradiation spots SP.

The beams of charged particles are extracted from the synchrotron by the technique disclosed in Patent Document 3. This technique is made up of applying high-frequency waves to circling beams (those beams of charged particles which circle in the synchrotron), thereby increasing their amplitude of betatron oscillation, and extracting from the synchrotron those beam particles with the large amplitude of betatron oscillation exceeding the stability limit. This technique keeps constant during extraction the parameters for operation of the extraction-related apparatus of the synchrotron, resulting in a high orbit stability for the beams of charged particles being extracted from the synchrotron and a high position accuracy for the irradiation beams.

Patent Document 1: Japanese Patent No. 2833602
Patent Document 2: Japanese Patent No. 3874766
Patent Document 3: Japanese Patent No. 2596292

It is essential for the spot scanning technique to achieve precision irradiation for treatment to accurately position the beams of charged particles and to accurately control the beam size. With this in mind, the present inventors carried out experiments to realize a method of precision irradiation for treatment by the particle beam therapy system with a synchrotron. The results of experiments revealed that the beams of charged particles which have just been extracted from the synchrotron are poor in the reproducibility of the beam size and also poor in the stability of the beam orbit. The foregoing results may be discussed as follows.

In actual operation of a synchrotron, the beams of charged particles which have been introduced from a pre-accelerator become unstable in the course of acceleration to a prescribed energy level. Such beam instability easily occurs when the charged particles are at a low energy level immediately after their injection into the synchrotron, on account of repulsions (space charge effect) between particles constituting the beams of charged particles. As the result of beam instability, part of beam particles steeply increase in the amplitude of oscillation (betatron oscillation) with respect to the design orbit while they are circling in the synchrotron. These particles are lost by collision with the walls of the vacuum duct and ancillary apparatus.

Figure 10:
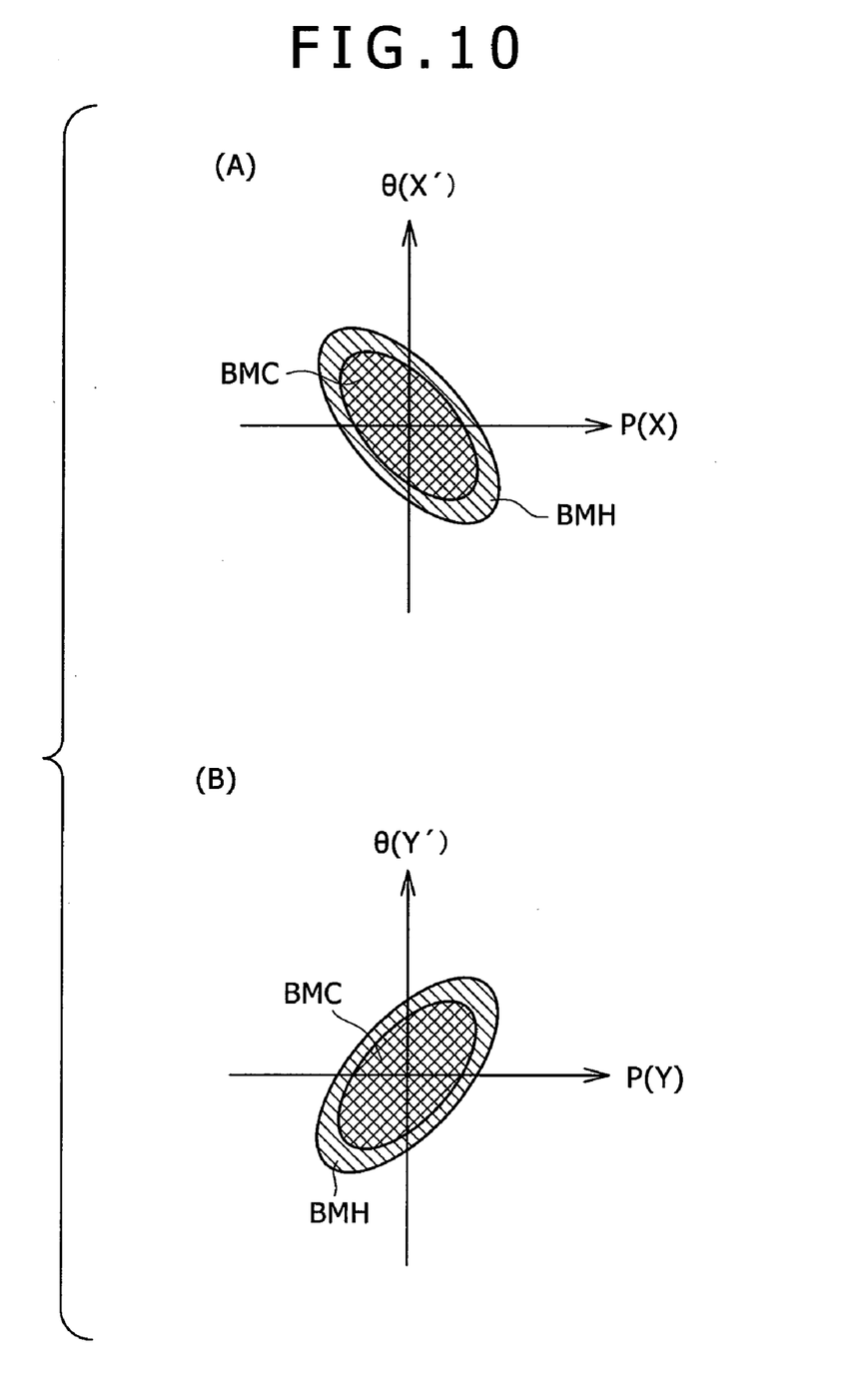
FIG. 10 is a diagram showing the phase space of the circling beams at the time of completion of synchrotron acceleration.

After acceleration to a prescribed energy level under the influence of beam instability, the beams of charged particles have the particle distribution in the phase space as shown in FIG. 10. The beam particles circle with betatron oscillation in the horizontal and vertical directions around the design orbit. FIG. 10(A) shows the phase space in the horizontal direction after completion of acceleration, and FIG. 10(B) shows the phase space in the vertical direction after completion of acceleration. The abscissa in FIG. 10 represents the deviation (position P) from the design orbit, and the ordinate in FIG. 10 represents the inclination (angle θ) toward the design orbit. The particle distribution in the beams of charged particles which have undergone acceleration has the core part at the center and the peripheral part called halo. The halo is formed by those beam particles which have increased in the amplitude of oscillation (emittance) in the horizontal and vertical directions under the influence of beam instability. The degree of halo formation has no reproducibility because the degree of beam instability has no reproducibility.

Ejection of beam particles from the synchrotron starts with those beam particles which have a large amplitude of betatron oscillation (emittance) and which have exceeded the stability limit. This suggests that beam particles forming halos (or halo-beam particles) are extracted first out of beam particles circling the synchrotron. This is a probable reason why the extracted beams (or the beams of charged particles extracted from the synchrotron) lacks good reproducibility in emittance immediately after extraction, and hence the reproducibility of the beam size and the stability of the beam orbit are poor in the irradiation apparatus immediately after the start of extraction from the synchrotron. The results of the present inventors' experiments revealed that the beam particles extracted from the synchrotron rapidly decrease in emittance with the lapse of time. A probable reason for this is that the extracted beams rapidly decrease in emittance as the extraction of halo-beam particles proceeds.

OBJECT AND SUMMARY OF THE INVENTION

It is an object of the present invention to provide a particle beam therapy system with a synchrotron, which produces irradiation beams suitable for high-precision particle beam therapy, with the irradiation beams accurately controlled for position and beam size.

In a primary aspect according to the present invention, a particle beam therapy system includes a synchrotron which accelerates beams of charged particles to a desired energy level and permits extraction of the beams of charged particles exceeding the stability limit, an irradiation device which irradiates an object with the beams of charged particles, a beam transport system which conducts the beams of charged particles extracted from the synchrotron to the irradiation device, and a control unit which works in such a way as to remove part of the beams of charged particles circling in the synchrotron and allow the rest of the circling beams of charged particles to be extracted from the synchrotron and conducted to the irradiation device.

To be specific, the particle beam therapy system is characterized in that the synchrotron has multi-pole electromagnets and the control unit controls the multi-pole electromagnets so as to reduce the stability limit and cause part of the beams of charged particles which has exceeded the reduced stability limit to be removed by the synchrotron or the beam transport system.

The particle beam therapy system is also characterized in that the synchrotron has an extraction device which alters the amplitude of betatron oscillation of the beams of charged particles, and the control unit controls the extraction device so as to increase the amplitude of the betatron oscillation and cause part of the beams of charged particles which has exceeded the stability limit to be removed by the synchrotron or the beam transport system.

The particle beam therapy system is also characterized in that the beam transport system has a bending electromagnet to generate a dipole magnetic field and, in the case where the beams of charged particles are removed by the beam transport system, the bending electromagnet removes part of the beams of charged particles extracted from the synchrotron.

The particle beam therapy system according to the aspect of the present invention permits the accurate positioning and beam size of the irradiation beams and the production of irradiation beams suitable for precision particle beam therapy.

BRIEF DESCRIPTION OF THE DRAWINGS

Embodiment(s) of the present invention will be described in detail based on the following figures, wherein.

DESCRIPTION OF THE PREFERRED EMBODIMENTS

The particle beam therapy system according to the present invention is realized by the embodiment which will be described below with reference to the accompanying drawings.

Example 1

Figure 1:
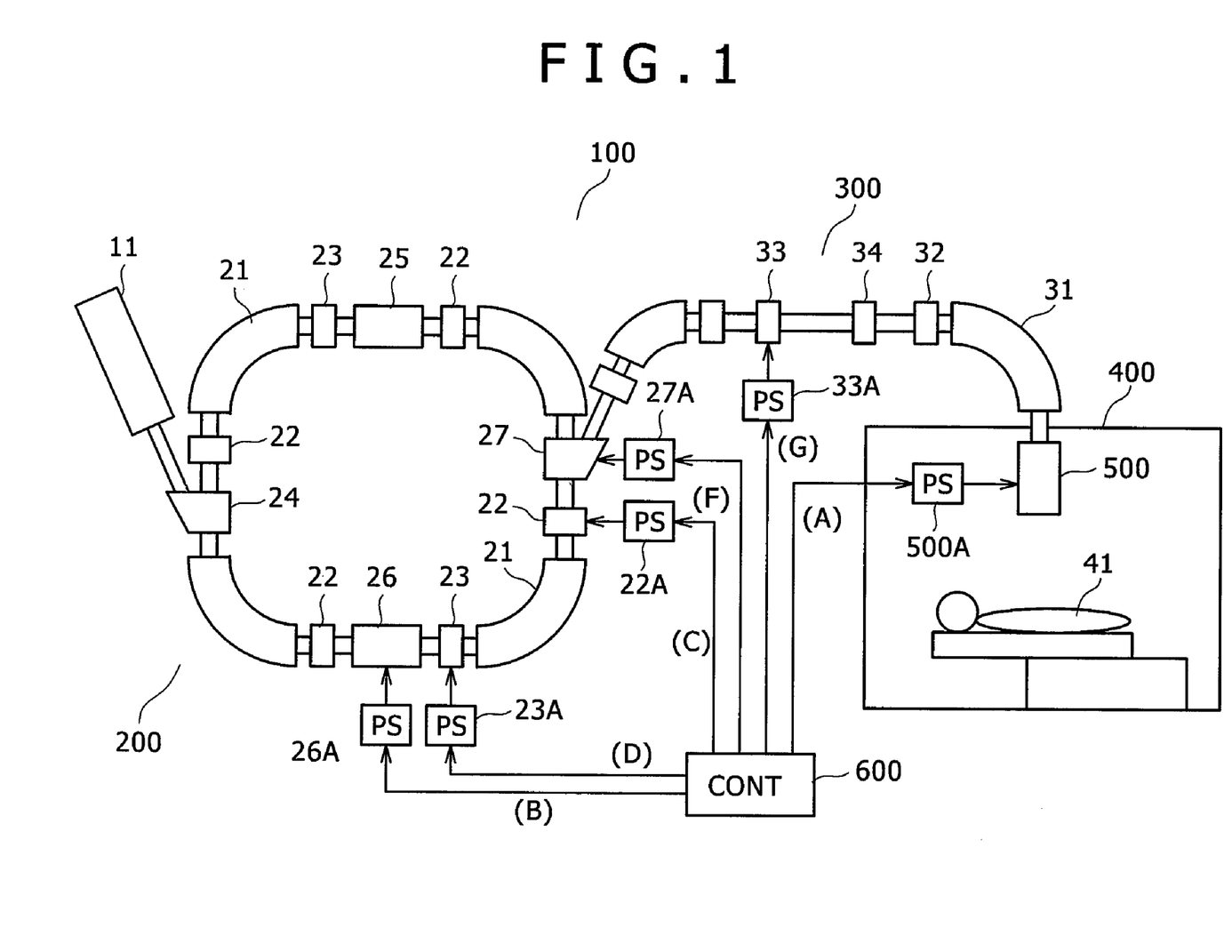
FIG. 1 is a diagram showing the construction of the particle beam therapy system according to Example 1.

This example demonstrates the particle beam therapy system constructed as shown in FIG. 1.

The particle beam therapy system 100 is composed of a synchrotron 200, a beam transport system 300, a treatment room 400, an irradiation device 500, and a control unit 600. The synchrotron 200 receives beams of charged particles which have been preaccelerated by a preaccelerator 11 such as a linac 11, and then it ejects them after acceleration to a certain energy level. The beam transport system 300 transports the outgoing beams from the synchrotron 200 to the treatment room 400. The irradiation device 500 directs the beams of charged particles to the affected part of a patient 41.

The synchrotron 200 is composed of the following components.

An injector 24 to inject beams of charged particles which have been preaccelerated by the preaccelerator 11.

Bending electromagnets 21 to deflect the beams of charged particles and cause them to circle along a predetermined orbit.

Quadrupole electromagnets 22 of convergence/divergence type to converge the beams of charged particles in the horizontal/vertical directions, thereby preventing them from spreading.

A power source 22A to excite the quadrupole electromagnets 22.

An acceleration cavity 25 to accelerate the beams of charged particles to a predetermined energy level by means of an RF accelerating voltage.

Sextupole electromagnets 23 to establish the stability limit for the amplitude of oscillation of the circling beams of charged particles.

A power source 23A to excite the sextupole electromagnets 23.

An extraction device 26 to produce an RF electromagnetic field which increases the amplitude of oscillation of the beams of charged particles and causes them to exceed the stability limit.

An RF power source 26A to supply the extraction device 26 with an RF electric power for ejection.

An extraction deflecting device 27 to generate an electrostatic field and a magnetostatic field which deflect the beams of charged particles, which have exceeded the stability limit, and cause them to be extracted from the synchrotron 200.

A high-voltage power source 27A to excite the extraction deflecting device 27.

The beam transport system 300 is composed of the following components.

A bending electromagnet 31 to generate a magnetic field to deflect and lead the outgoing beams from the synchrotron 200 to the treatment room 400 along a predetermined orbit.

A quadrupole electromagnets 32 of convergence/divergence type to converge the beams of charged particles in the horizontal/vertical directions, thereby preventing them from spreading during transport.

A beam shielding electromagnet 33 to turn on and off the supply of the beams of charged particles to the irradiation device 500 in the treatment room.

A power source 33A to excite the beam shielding electromagnet 33.

A beam dump 34 to discard the beam component removed by the beam shielding electromagnet.

The beam shielding electromagnet 33 is a bending electromagnet to generate a dipole magnetic field. It causes the excited dipole magnetic field to deflect unnecessary beam components and causes the beam dump 34 to discard them. Alternatively, it deflects the beams by the excited dipole magnetic field and supplies only the deflected beam components to the irradiation device 500. The former procedure merely needs simple adjustment for the beam transport system, and the latter procedure assures safety because the supply of the beams of charged particles to the irradiation device 500 is interrupted when anomaly occurs in the equipment.

Figure 9:
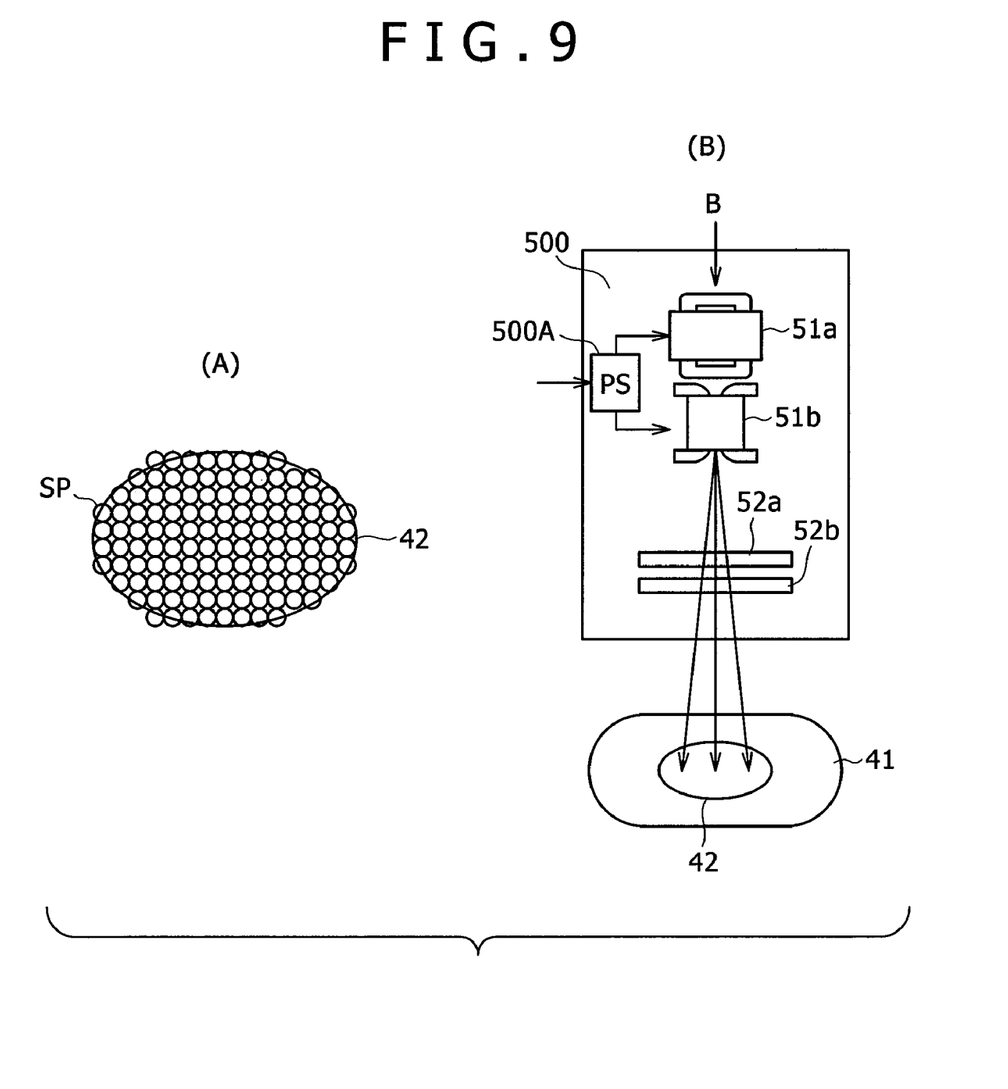
FIG. 9 is a diagram illustrating the method for spot scanning irradiation. Part (A) is a diagram showing one layer of the affected part divided in the depthwise direction, as viewed from the upstream side of the irradiation beam. Part (B) is a front view showing the construction of the irradiation device attached to the particle beam therapy system.

The irradiation device 500 is composed of the following components as shown in FIG. 9(B).

Scanning electromagnets 51a and 51b to deflect in the horizontal and vertical directions the beams of charged particles, which have been introduced by the beam transport system 300, and to scan them two-dimensionally in conformity with the cross section of the affected part 42.

A power source 500A to excite the scanning electromagnets 51a and 51b.

Monitors 52a and 52b to watch the position, size (shape), and dose of the beams of charged particles.

The control unit 600 is connected to the power source 22A for the quadrupole electromagnets 22, the RF power source 26A to supply the extraction device 26 with an RF electric power for extraction, the high-voltage power source 27A for the extraction deflecting device 27, the power source 33A for the beam shielding electromagnet 33, and the power source 500A for the scanning electromagnets 51a and 51b, for their control.

The particle beam therapy system according to this example employs the spot scanning method for irradiation. This method will be described below with reference to FIGS. 9(A) and 9(B). FIG. 9(A) shows one layer of the affected part which has been divided depthwise, as viewed from the upstream side of the beams of charged particles for irradiation. The irradiation spots (SP) are defined by dividing the three-dimensional affected part depthwise into layers and further dividing each layer two-dimensionally. Each layer for irradiation is selected by adjusting the energy of irradiation beams or the energy of extracted beams from the synchrotron 200. Then, each layer is two-dimensionally scanned with the irradiation beams by means of the scanning electromagnets 51 so that each irradiation spot (SP) is given a predetermined dose, as shown in FIG. 9(A). As soon as one irradiation spot (SP) has received a predetermined dose, the irradiation beams are cut off rapidly and the direction of irradiation is moved to the next irradiation spot (SP), with the irradiation beams cut off. And irradiation is resumed and repeated in the same way as mentioned above.

Figure 2:
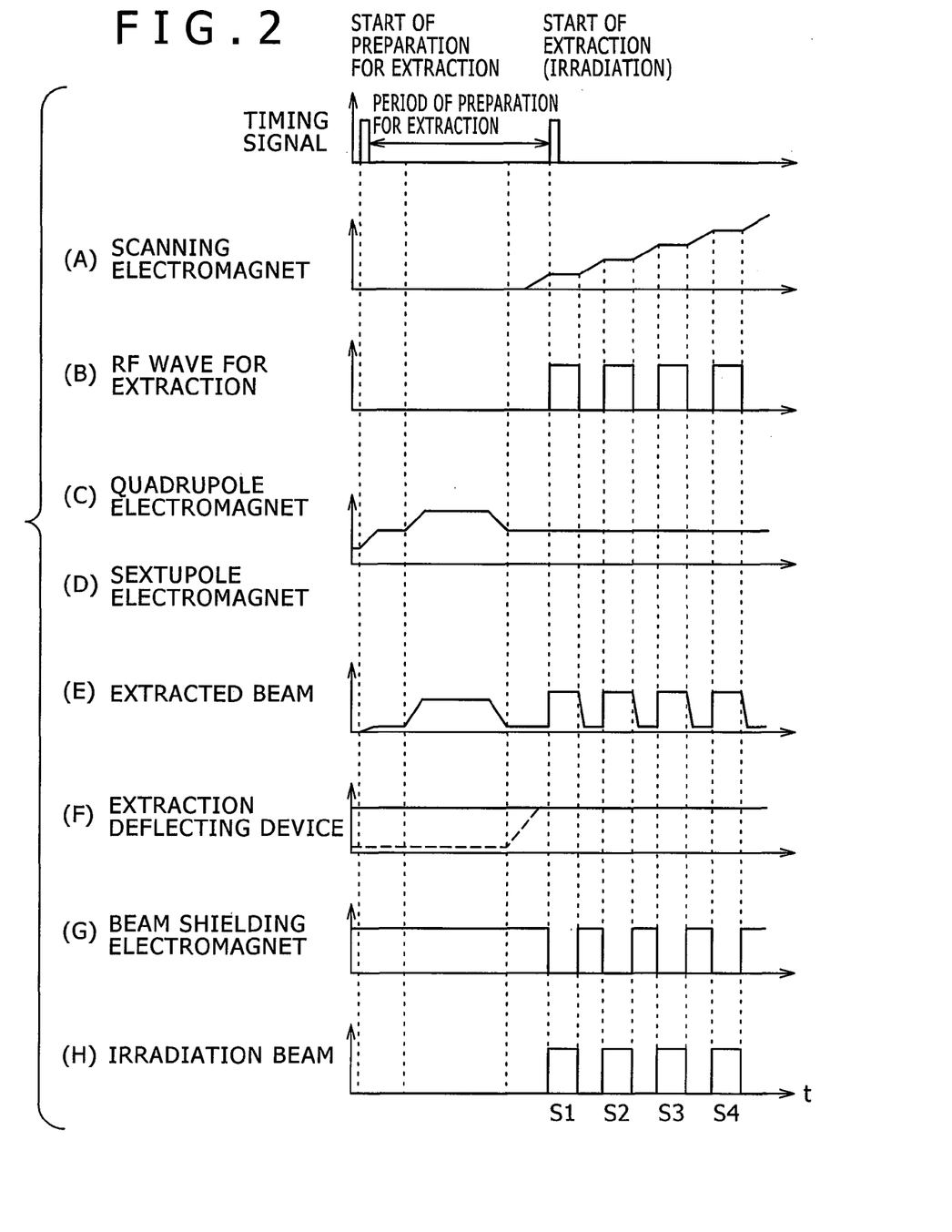
FIG. 2 is a timing chart showing the operation sequence of the particle beam therapy system according to Example 1.

The particle beam therapy system according to this example is run according to the operation sequence which will be described below with reference to FIG. 2. FIG. 2 shows the extraction preparing period that follows the completion of synchrotron acceleration and the timing chart immediately after the start of extraction (or irradiation).

In FIG. 2, the abscissa represents time (t). In FIG. 2(A), the ordinate represents the exciting current to be supplied to the scanning electromagnet 51 from the exciting power source 500A in response to the scanning instruction signal which is transmitted from the control unit 600 to the exciting power source 500A for the scanning electromagnet 51. In FIG. 2(B), the ordinate represents the RF electric power for extraction to be supplied to the extraction device 26 from the RF power source 26A in response to the RF control signals for extraction which is transmitted to the RF power source 26A for the extraction device 26 from the control unit 600. In FIGS. 2(C) and 2(D), the ordinate represents the exciting current to be supplied to the quadrupole electromagnet 22 from the exciting power source 22A in response to the exciting current control signals which are supplied to the exciting power source 22A for the quadrupole electromagnet 22 from the control unit 600. Likewise, it also represents the exciting current to be supplied to the sextupole electromagnet 23 from the exciting power source 23A. In FIG. 2(E), the ordinate represents the amount of the beams of charged particles which are extracted from the synchrotron. In FIG. 2(F), the ordinate represents the exciting current or applied voltage to be supplied to the extraction deflecting device 27 from the exciting power source 27A in response to the control signals which are transmitted to the exciting power source (or high-voltage power source) for the extraction deflecting device 27 from the control unit 600. In FIG. 2(G), the ordinate represents the sequence in which the beam shielding electromagnet 33 is turned on and off in response to the control signals which are transmitted to the exciting power source 33A for the beam shielding electromagnet 33 from the control unit 600. In FIG. 2(H), the ordinate represents the sequence in which the irradiation beams (from the irradiation device 500) are turned on and off. The irradiation beams sequentially form spot S1, spot S2, spot S3, spot S4, . . . as they are turned on.

As shown in FIG. 2(A), the exciting current supplied to the scanning electromagnets 51 from the exciting power source 500A is increased for the irradiation beams to scan the irradiation positions. The exciting current supplied to the scanning electromagnets 51 from the exciting power source 500A is kept constant for the irradiation beams to stay at a fixed irradiation position. The spot scanning method is applied in such a way that one irradiation spot (SP) is irradiated in a prescribed dose, with the scanning electromagnet 51 excited at a prescribed level and the scanning of the beams of charged particles suspended, and then the adjacent irradiation spot (SP) is irradiated, with the irradiation beams turned off and the scanning electromagnet 51 excited at a different level, as shown in FIGS. 2(A) and 2(H).

After the start of extraction (or irradiation), the RF electromagnetic field to be applied to the extraction device 26 is turned on at the time of spot irradiation during which the beams of charged particles are supplied to the irradiation device 500, and the RF electromagnetic field to be applied to the extraction device 26 is turned off at the time of movement from one spot to another during which the supply of the beams of charged particles to the irradiation device 500 is interrupted, as shown in FIG. 2(B). At the same time as the supply of the beams of charged particles to the irradiation device 500 is interrupted, the beam shielding electromagnet 33 attached to the irradiation device 500 is turned on to interrupt the supply of the beams of charged particles, as shown in FIG. 2(G).

The process in this example is carried out in such a way that beam particles circling in the synchrotron 200 are rectified by the removal of halo-beam particles (or those beam particles that form halos) in the extraction preparation period. To be specific, the quadrupole electromagnets 22 or sextupole electromagnets 23 in the synchrotron 200 are excited in the extraction preparing period as shown in FIGS. 2(C) and 2(D). Controlling the multi-pole electromagnets (quadrupole electromagnets 22 or sextupole electromagnets 23) alters the stability limit. Increasing the amount of excitation of the quadrupole electromagnets 22 or sextupole electromagnets 23 reduces the stability limit, thereby creating a situation in which those beam particles circling in the synchrotron 200 which have a large amplitude of betatron oscillation exceed the stability limit. The halo-beam particles which have a large amplitude of betatron oscillation exceed the stability limit. The extraction deflecting device 27 is excited in the extraction preparing period as shown by the solid line in FIG. 2(F), and this applies the static electric field and static magnetic field and causes those beam particles which have exceeded the stability limit to be extracted from the synchrotron 200 and conducted to the beam transport system 300. Since the beam shielding electromagnet 33 is excited in the extraction preparing period as shown in FIG. 2(F), the beam particles which have been conducted into the beam transport system 300 are deflected from the design orbit and removed as the result of collision with the beam dump 34. Since the beam particles which have been extracted from the synchrotron 200 in the extraction preparing period are removed in the beam transport system 300, they are not supplied to the irradiation device 500 and hence no beams are ejected from the irradiation device 500 as shown in FIG. 2(H).

Being small in amount, halo-beam particles can be removed inside the synchrotron 200 if the static electric and magnetic fields to be applied to the extraction deflecting device 27 are turned off in the extraction preparing period, as indicated by the dotted line in FIG. 2(F). Removing the beams of charged particles inside the beam transport system offers the advantage of preventing the apparatus from becoming radioactive. Removing the beams of charged particles inside the synchrotron 200 offers the advantage of improving safety in that unnecessary beams are not supplied to the irradiation device 500 because the extraction deflecting device 27 is turned off at the same time.

Figure 3:
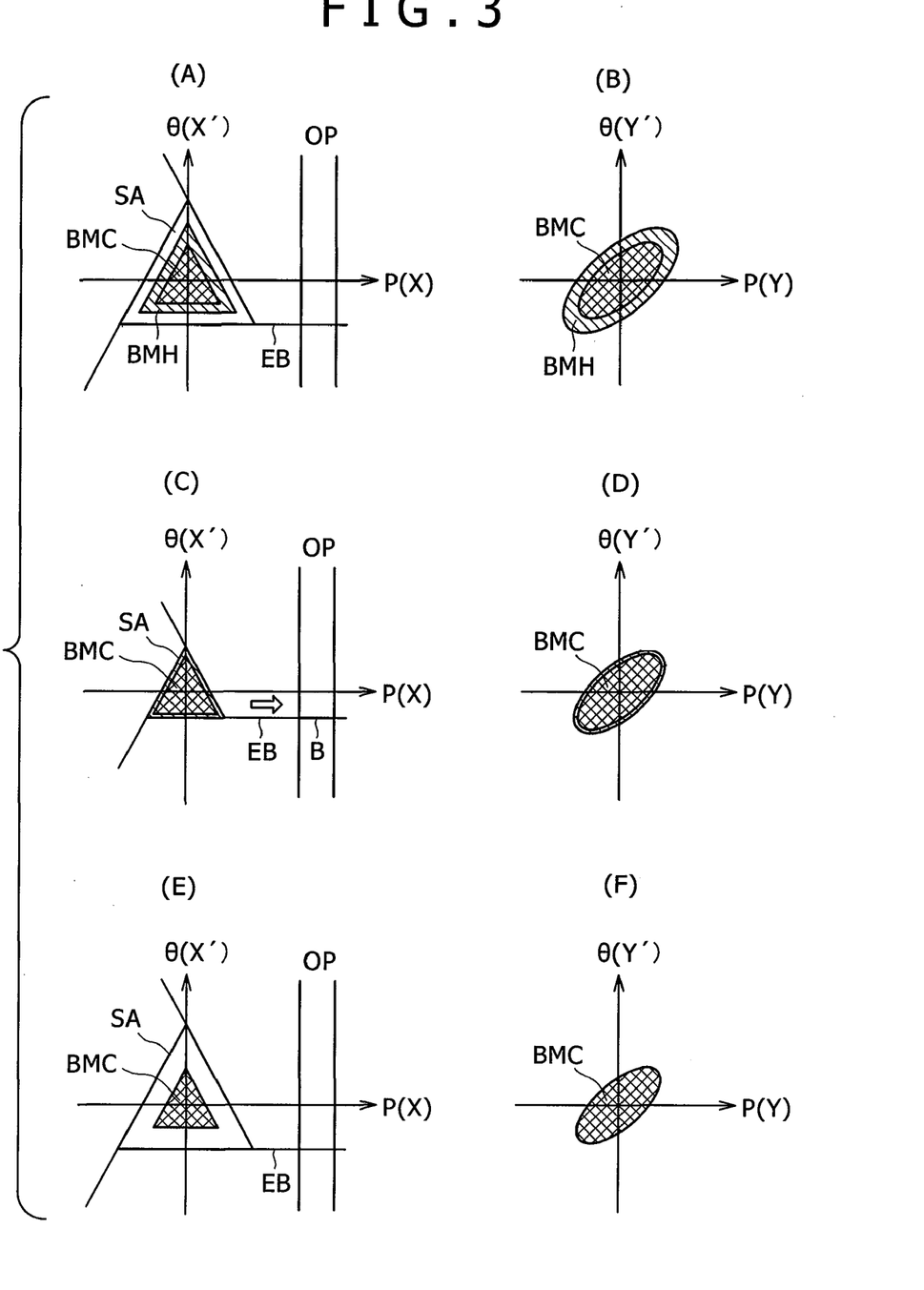
FIG. 3 is a diagram showing the principle of the method for removing halo-beam particles according to Example 1.

Removal of halo-beam particles inside the beam transport system in the extraction preparing period is accomplished based on the principle which is described below with reference to FIG. 3. Individual beam particles constituting the beams of charged particles circle (in the form of circling beam BM) around the center of the design orbit, with betatron oscillation in the horizontal and vertical directions. FIG. 3 shows the state of the beams of charged particles circling inside the synchrotron 200, in the horizontal phase space (relating to extraction) and in the vertical phase space (perpendicular to the horizontal direction). The abscissa represents the deviation (position P) from the design orbit, and the ordinate represents the gradient (angle θ) with respect of the design orbit.

FIG. 3(A) shows the phase space in the horizontal direction prior to removal of halo-beam particles, and FIG. 3(B) shows the phase space in the vertical direction prior to removal of halo-beam particles. The sextupole electromagnet 23 in its excited state forms the triangular stable region SA in the phase space in the horizontal direction, as shown in FIG. 3(A). In the phase space for the beams of charged particles are distributed circling beams BMC forming the core at the center and are also distributed circling beams BMH consisting of halo-beam particles around the core. Beam particles within the stable region continue to stably circle inside the synchrotron 200. By contrast, beam particles outside the stable region steeply increase in the amplitude of betatron oscillation along the extraction branch, and eventually they enter the opening OP of the extraction deflecting device 27 for extraction from the synchrotron 200. Prior to removal of halo-beam particles, the size of the stable region SA is so established as to be larger than the emittance (area occupied in the phase space) of beam particles. The circling beams BMC forming the core and the circling beams BMH consisting of halo-beam particles, which are within the stable region SA, stably circle inside the synchrotron 200.

The size of the stable region SA is determined by the amount of excitation for the quadrupole electromagnets 22 and the sextupole electromagnets 23. With increased excitation, the stable region SA reduces as shown in FIG. 3(C). FIG. 3(C) shows the phase space (in the horizontal direction) during removal of halo-beam particles, and FIG. 3(D) shows the phase space (in the vertical direction) during removal of halo-beam particles. The amount of excitation for the quadrupole electromagnets 22 and the sextupole electromagnets 23 is adjusted to reduce the stability limit, thereby expelling halo-beam particles from the stability region SA. Those halo-beam particles which have exceeded the stability limit are extracted from the synchrotron 200. The thus extracted beams B are removed by the beam transport system 300.

After removal of halo-beam particles, the amount of excitation of the quadrupole electromagnets 22 and sextupole electromagnets 23 is adjusted again so that the stability limit is extended as much as necessary, as shown in FIG. 3(E). In the stability region SA remain the circling beams BMC.

After start of extraction (irradiation), an RF electromagnetic field for extraction is applied to the extraction device 26, as shown in FIG. 2(B). The application of an RF electromagnetic field for extraction causes the circling beams BMC within the stable region SA to increase in emittance in the horizontal direction (which results in an increase in the amplitude of oscillation of beam particles). Since the extraction deflecting device 27 is on, those beam particles exceeding the stability limit are extracted from the synchrotron 200 and conducted to the beam transport system 300. Since the beam shielding electromagnet 33 is off, those beam particles extracted from the synchrotron 200 proceed along the beam transport system 300 and reach the irradiation device 500. As the RF electromagnetic field being applied to the extraction device 26 is turned off, extraction of beam particles from the synchrotron 200 is suspended. That is, turning on and off the RF electromagnetic field for the extraction device 26 controls the extraction of beam particles from the synchrotron 200, and turning on and off the beam shielding electromagnet 33 controls the irradiation beams from the irradiation device 500.

This example produces the following effects. The particle beam therapy system according to this example removes halo-beam particles (as a part of the beams of charged particles circling around the synchrotron) prior to the start of irradiation, which improves the reproducibility of the beam size immediately after the start of irradiation and the stability of the beam orbit. This in turn leads to the accurate positioning and beam size of the irradiation beams and the production of irradiation beams suitable for precision particle beam therapy such as spot scanning applicable to affected parts in complex shape.

Example 2

This example demonstrates another example of the particle beam therapy system according to the present invention. The particle beam therapy system in this example is identical in construction with that in Example 1 as shown in FIG. 1 but is different in operation sequence from that in Example 1.

Figure 4:
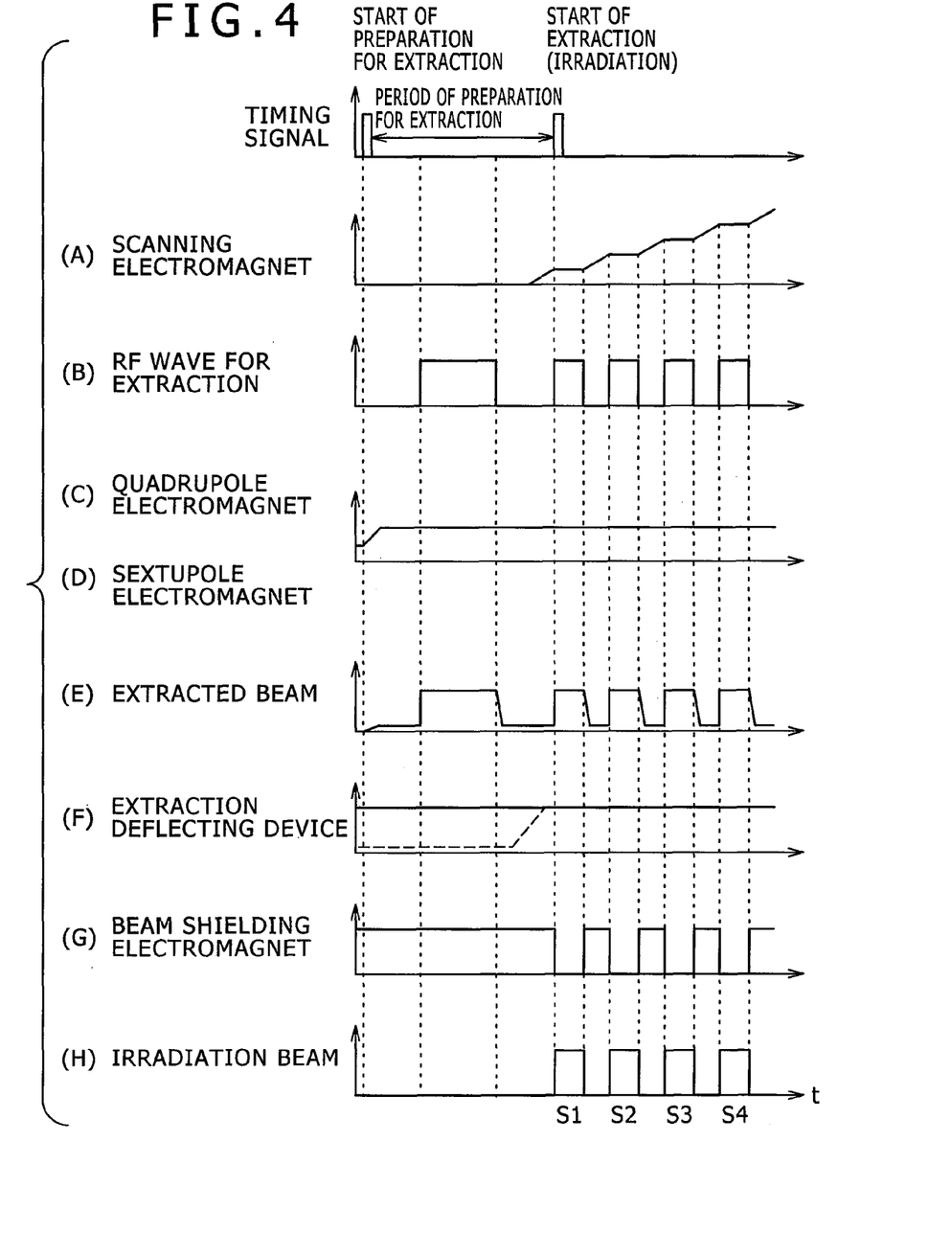
FIG. 4 is a timing chart showing the operation sequence of the particle beam therapy system according to Example 2.

The particle beam therapy system according to this example is run according to the operation sequence which is described below with reference to FIG. 4. FIG. 4 shows the extraction preparing period that follows the completion of synchrotron acceleration and the timing chart immediately after the start of extraction, which are applicable to the spot scanning method for irradiation. The difference from Example 1 is the method for removal of halo-beam particles in the distribution of the beams of charged particles after the completion of acceleration. In FIG. 4, the abscissa represents time (t). The ordinates in FIGS. 4(A) to 4(H) are identical respectively with those in FIGS. 2(A) to 2(H).

In this example, the particle beam therapy system is run in such a way that the quadrupole electromagnets 22 and sextupole electromagnets 23 for the synchrotron 200 are excited at a substantially constant level in the extraction preparing period, as shown in FIGS. 4(C) and 4(D). Excitation in this manner keeps the stability limit constant. By contrast, the application of an RF electromagnetic field to the extraction device 26 in the extraction preparing period shown in FIG. 4(B) (which increases the amplitude of betatron oscillation of circling beams in the horizontal direction) causes halo-beam particles (with an increased amplitude of betatron oscillation in the horizontal direction) to exceed the stability limit. As in Example 1, those halo-beam particles which have exceeded the stability limit are removed from the synchrotron 200 and conducted to the beam transport system 300 by the extraction deflecting device 27 and then removed by the beam shielding electromagnet 33. The halo-beam particles, which are small in amount, can be made to disappear in the synchrotron 200 by turning off the static electric and magnetic fields for the extraction deflecting device 27, as indicated by the broken line in FIG. 4(F).

Figure 5:
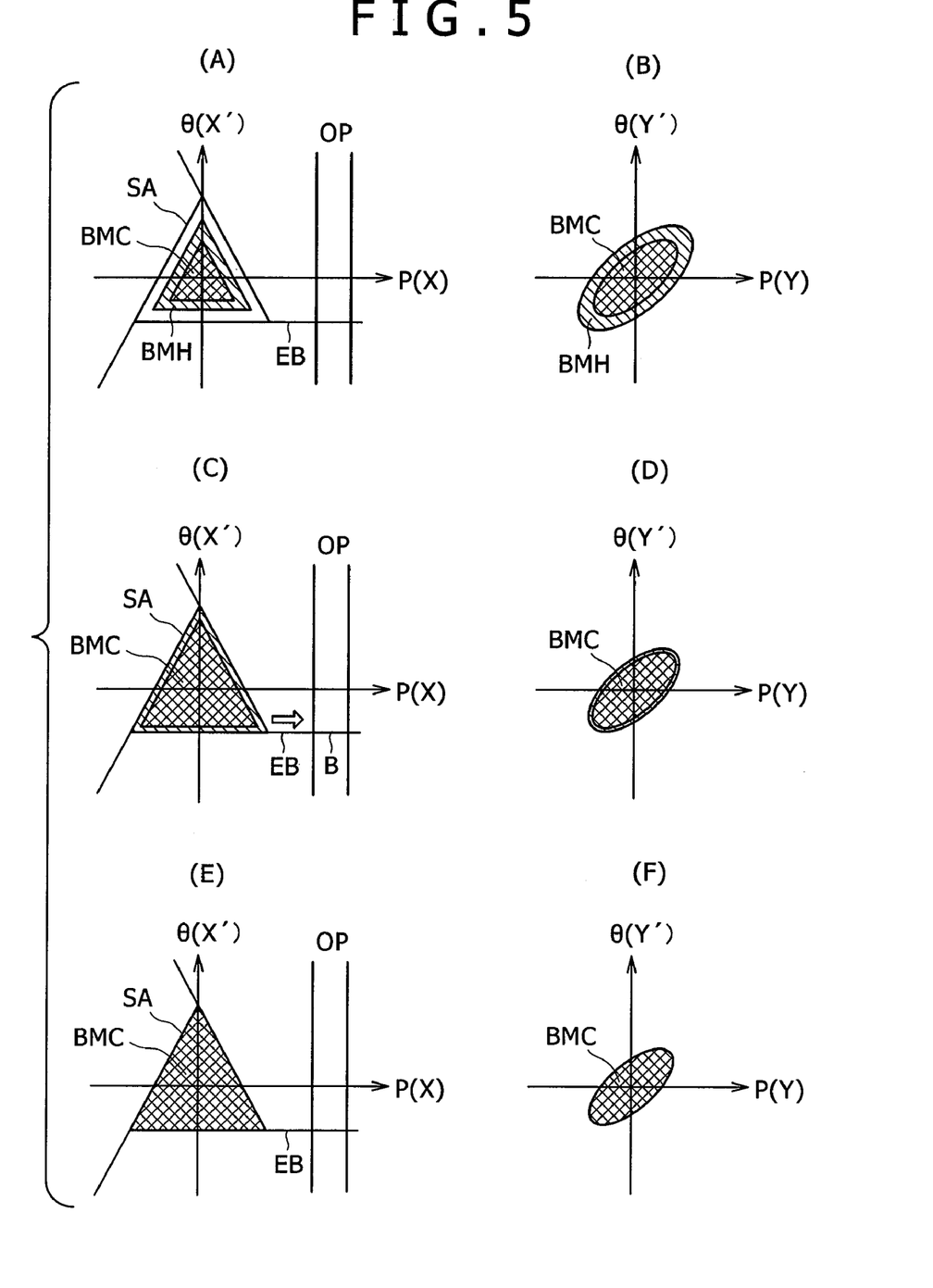
FIG. 5 is a diagram showing the principle of the method for removing halo-beam particles according to Example 2.

Removal of halo-beam particles in the extraction preparing period is accomplished based on the principle which is described below with reference to FIG. 5. FIG. 5(A) shows the phase space in the horizontal direction prior to removal of halo-beam particles, and FIG. 5(B) shows the phase space in the vertical direction prior to removal of halo-beam particles. In the phase space after completion of acceleration, circling beams BMC forming the core are distributed at the center, and circling beams BMH consisting of halo-beam particles are distributed in the peripheral region. The amount of excitation for the quadrupole electromagnets 22 and sextupole electromagnets 23 is established such that the stable region SA is larger than the emittance (area occupied in the phase space) of the beams of charged particles prior to removal of halo-beam particles. Since the circling beams BMC and the circling beams BMH are distributed within the stable region SA as shown in FIG. 5(A), they stably circle inside the synchrotron 200.

Halo-beam particles are removed by application of an RF electromagnetic field to the extraction device 26 for beam particles to increase in emittance (amplitude of betatron oscillation) in the horizontal direction. FIG. 5(C) shows the phase space in the horizontal direction during removal of halo-beam particles, and FIG. 5(D) shows the phase space in the vertical direction during removal of halo-beam particles. Those halo-beam particles which have exceeded the stability limit are extracted from the synchrotron 200 and then removed by the beam transport system 300.

FIG. 5(E) shows the phase space in the horizontal direction after removal of halo-beam particles, and FIG. 5(F) shows the phase space in the vertical direction after removal of halo-beam particles. After removal of halo-beam particles, the circling beams BMC are distributed within the stable region SA. In other words, they stably circle inside the synchrotron 200.

After the start of extraction (irradiation), the same control as in Example 1 is carried out. That is, circling beams BMC are extracted from the synchrotron 200 and the irradiation beams from the irradiation device 500 are turned on and off. This example produces the same effect as Example 1.

Example 3

Figure 6:
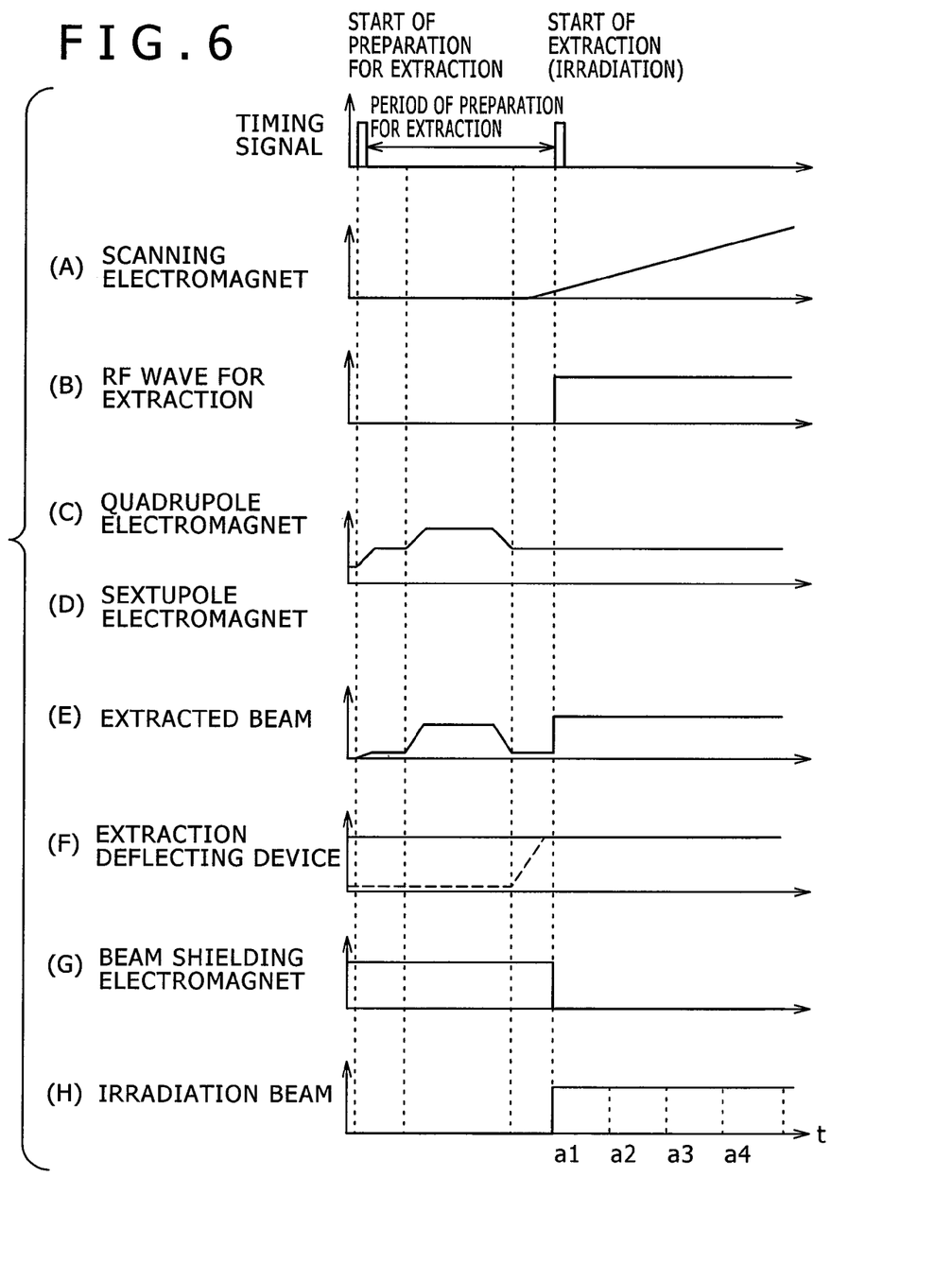
FIG. 6 is a timing chart showing the operation sequence of the particle beam therapy system according to Example 3.

This example demonstrates another example of the particle beam therapy system according to the present invention. The particle beam therapy system in this example employs the raster scanning method for irradiation. It is identical in construction with that in Example 1 as shown in FIG. 1. The operation sequence used in this example is described below with reference to FIG. 6. FIG. 6 shows the extraction preparing period that follows the completion of synchrotron acceleration and the timing chart immediately after the start of extraction. The same method as in Example 1 (for spot scanning) is used in this example to remove halo-beam particles distributing in the beams of charged particles after the completion of acceleration. In FIG. 6, the abscissa represents time (t). The ordinates in FIGS. 6(A) to 6(H) are identical respectively with those in FIGS. 2(A) to 2(H).

In this example, the particle beam therapy system is run in such a way that the quadrupole electromagnets 22 and sextupole electromagnets 23 for the synchrotron 200 are excited in varied amounts in the extraction preparing period, as shown in FIGS. 4(C) and 4(D). Excitation in this manner reduces the stability limit, so that halo-beam particles distributing in the beams of charged particles with a large amplitude of betatron oscillation exceed the stability limit. And those beam particles exceeding the stability limit are extracted from the synchrotron 200 by means of the extraction deflecting device 27 and then conducted to the beam transport system 300 for removal by the beam shielding electromagnet 33.

Incidentally, the halo-beam particles, which are small in amount, can be made to disappear in the synchrotron 200 by turning off the static electric and magnetic fields for the extraction deflecting device 27, as indicated by the broken line in FIG. 6(F).

The raster scanning method is described below. It is similar to the spot scanning method (shown in FIG. 9) in that the three-dimensional affected part is divided into several layers in the depthwise direction and each layer is further divided two-dimensionally into small regions a1, a2, a3, a4, . . . (which correspond to the irradiation spots). Each layer (in the depthwise direction) is selectively irradiated by adjusting the energy of beams extracted from the synchrotron 200 (or the energy of irradiation beams). In each layer, the small regions a1, a2, a3, a4, . . . are scanned sequentially and two-dimensionally with the irradiation beam (in a desired dose) directed by the scanning electromagnet 51. The raster scanning method is characterized in that the irradiation beam is kept on while it moves from one small region to another. That is, the amount of excitation for the scanning electromagnet 51 is continuously changed after the start of extraction (or irradiation), as shown in FIG. 6(A), and an RF electromagnetic field is applied continuously to the extraction device 26, so that continuous irradiation is carried out with the extracted beams from the synchrotron 200. This is the difference in operation sequence between the raster scanning method and the spot scanning method.

The raster scanning method of this example also produces the same effect as Example 1. That is, like the spot scanning method, it removes halo-beam particles in the extraction preparing period, which improves the reproducibility and stability of the beam size immediately after the start of irradiation and also improves the accuracy of irradiation.

Example 4

Figure 7:
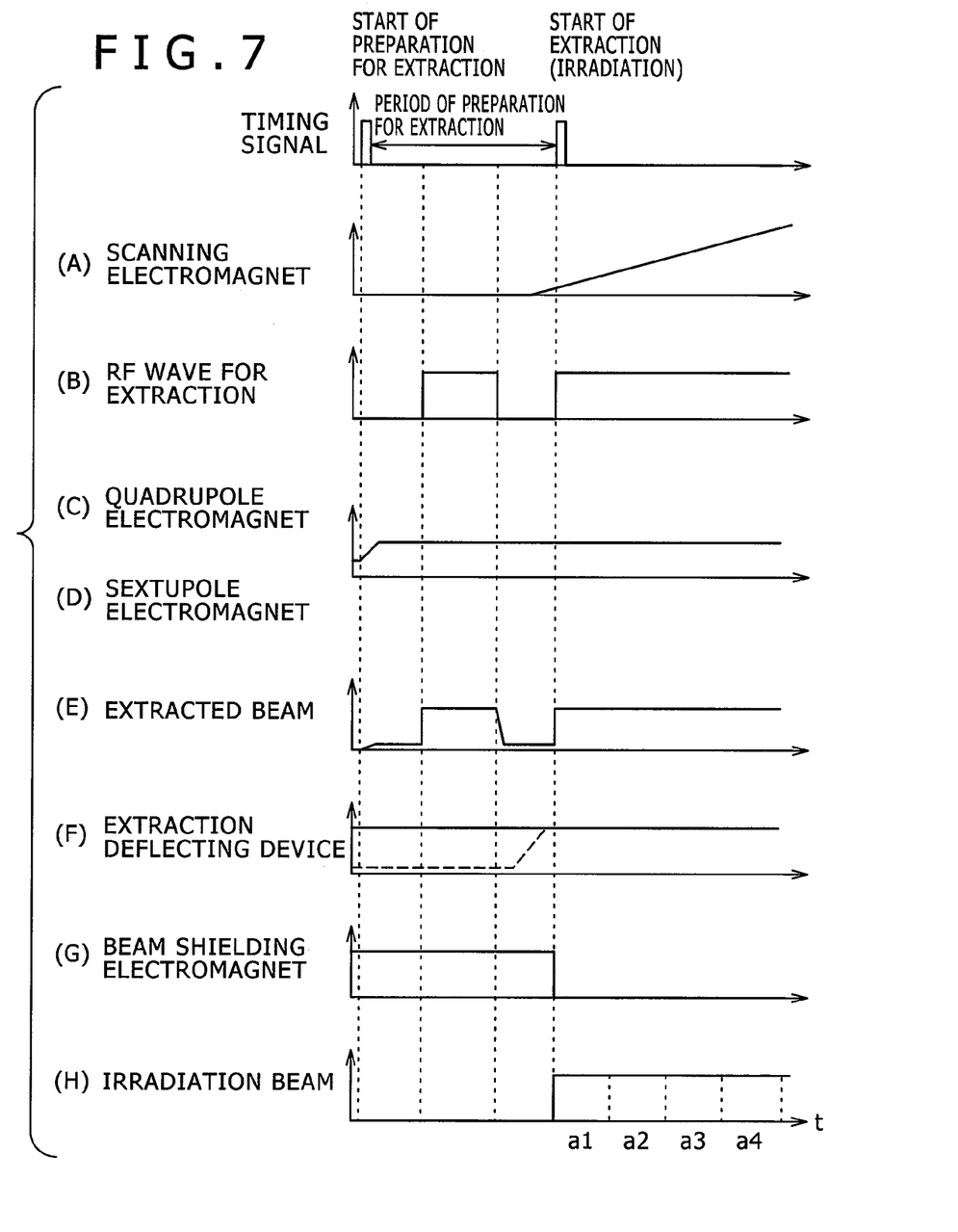
FIG. 7 is a timing chart showing the operation sequence of the particle beam therapy system according to Example 4.

This example demonstrates further another example of the particle beam therapy system according to the present invention. The particle beam therapy system in this example employs the raster scanning method for irradiation. It is identical in construction with that in Example 1 as shown in FIG. 1. The operation sequence used in this example is described below with reference to FIG. 7. FIG. 7 shows the extraction preparing period that follows the completion of synchrotron acceleration and the timing chart immediately after the start of extraction. The same method as in Example 2 (for spot scanning) is used in this example to remove halo-beam particles distributing in the beams of charged particles after the completion of acceleration. In FIG. 7, the abscissa represents time (t). The ordinates in FIGS. 7(A) to 7(H) are identical respectively with those in FIGS. 2(A) to 2(H).

In this example, the particle beam therapy system is run in such a way that the quadrupole electromagnets 22 and sextupole electromagnets 23 for the synchrotron 200 are excited at a constant level (so that the stability limit is kept constant) in the extraction preparing period, as shown in FIGS. 7(C) and 7(D). On the other hand, an RF electromagnetic field is applied to the extraction device 26 in the extraction preparing period, as shown in FIG. 7(B), so as to increase the amplitude of betatron oscillation of circling beams in the horizontal direction. Halo-beam particles (with an increased amplitude of betatron oscillation in the horizontal direction) exceed the stability limit. As in Example 1, those halo-beam particles which have exceeded the stability limit are removed from the synchrotron 200 and conducted to the beam transport system 300 by the extraction deflecting device 27 and then removed by the beam shielding electromagnet 33.

The halo-beam particles, which are small in amount can be made to disappear in the synchrotron 200 by turning off the static electric and magnetic fields for the extraction deflecting device 27, as indicated by the broken line in FIG. 7(F). This example produces the same effect as Example 1.

The present invention will be applied not only to the particle beam therapy system for cancer treatment but also to physical researches involving the irradiation of a target with beams of high-energy charged particles accelerated by a synchrotron which needs a high precision and a desired intensity distribution.

It should be understood by those skilled in the art that various modifications, combinations, sub-combinations and alterations may occur depending on design requirements and other factors insofar as they are within the scope of the appended claims or the equivalents thereof.

What is claimed is:

1. A particle beam therapy system comprising:
   a synchrotron which accelerates beams of charged particles to a desired energy level and permits extraction of said beams of charged particles exceeding a stability limit during an extraction preparation period;
   an irradiation device which irradiates an object with said beams of charged particles during an extraction period;
   a beam transport system which conducts said beams of charged particles extracted from said synchrotron to said irradiation device; and
   a control unit which controls said synchrotron or said beam transport system to remove a first part of said beams of charged particles which exceed said stability limit in said synchrotron during the extraction preparation period, and allow a second part of said beams of charged particles to be extracted from said synchrotron and conducted to said irradiation device during the extraction period.

2. The particle beam therapy system as defined in claim 1, wherein
   said synchrotron has multi-pole electromagnets, and
   said control unit controls said multi-pole electromagnets so as to reduce said stability limit and cause said first part of said beams of charged particles which exceed said reduced stability limit to be removed by said synchrotron or said beam transport system.

3. The particle beam therapy system as defined in claim 1, wherein
   said synchrotron has an extraction device which alters an amplitude of betatron oscillation of said beams of charged particles, and
   said control unit controls said extraction device so as to increase said amplitude of said betatron oscillation and cause said first part of said beams of charged particles which exceed said stability limit to be removed by said synchrotron or said beam transport system.

4. The particle beam therapy system as defined in claim 1, wherein
   said beam transport system has a bending electromagnet to generate a dipole magnetic field, and
   said bending electromagnet is used to remove said first part of said beams of charged particles.

5. The particle beam therapy system as defined in claim 1, wherein
   said first part of said beams of charged particles in said synchrotron includes halo-beam particles.

* * * * *